United States Patent [19]

Heggie et al.

[11] Patent Number: 6,143,161
[45] Date of Patent: Nov. 7, 2000

[54] PROCESS FOR THE PREPARATION OF 4-(DES-DIMETHYLAMINO)-TETRACYCLINES

[75] Inventors: William Heggie, Palmela; José Galindro, Lisboa; Pedro Santos, Queluz; Luis Carvalho, Seixal, all of Portugal

[73] Assignee: Hovione Inter Ltd., Portugal

[21] Appl. No.: 09/317,396

[22] Filed: May 24, 1999

[30] Foreign Application Priority Data

May 26, 1998 [PT] Portugal ................................. 102160

[51] Int. Cl.[7] ............................................. C25B 3/00
[52] U.S. Cl. ........................ 205/437; 205/438; 205/446
[58] Field of Search .................................... 205/431, 437, 205/438, 447, 452, 453, 454, 456

[56] References Cited

U.S. PATENT DOCUMENTS

| | | | |
|---|---|---|---|
| 5,532,227 | 7/1996 | Golub et al. | 514/152 |
| 5,552,297 | 9/1996 | Wong et al. | 435/26 |

FOREIGN PATENT DOCUMENTS

| | | |
|---|---|---|
| 38201/93 | 10/1993 | Australia . |
| 0435362B1 | 7/1991 | European Pat. Off. . |
| 0586020A1 | 3/1994 | European Pat. Off. . |
| 0599397A1 | 6/1994 | European Pat. Off. . |
| 2136138 | 12/1972 | France . |
| 06009523 | 1/1994 | Japan . |
| 92/13515 | 8/1992 | WIPO . |
| 98/08480 | 3/1998 | WIPO . |

OTHER PUBLICATIONS

"Chemistry of the Tetracycline Antibiotics. I. Quaternary Derivatives"; James H. Boothe, et al.; J. Amer. Chem Soc.; Apr. 5, 1958; vol. 80; pp. 1654–1657.

"The Structure of Aureomycin"; C.R. Stephens, et al.; *J. Amer. Chem. Soc.*; Jul. 5, 1954; vol. 76; pp. 3568–3575.

Thanase et al., Optimized Electroanalysis of Tetracycline by Alternating Current Polarography, 1996, No month available Analusius, 24(7), 281–284.

*Primary Examiner*—Kathryn Gorgos
*Assistant Examiner*—Christopher Keehan
*Attorney, Agent, or Firm*—Ostrolenk, Faber, Gerb & Soffen, LLP

[57] ABSTRACT

The present invention refers to a process for the preparation of 4-(des-dimethylamino)-tetracyclines, which compounds have a therapeutical application. The starting tetracyclines are treated with a methylating agent and the resulting trimethylammonium salts are reduced by electrolysis in an aqueous solution at acidic pH, in the presence of an adequate electrolyte. A direct electrical current with a potential of 0.5–1.5 volts is applied between two convenient electrodes until the reaction is complete. The 4-(des-dimethylamino)-tetracyclines are isolated by extraction with an organic solvent.

14 Claims, No Drawings

PROCESS FOR THE PREPARATION OF 4-(DES-DIMETHYLAMINO)-TETRACYCLINES

The present invention refers to a new process for the preparation of 4-(des-dimethylamino)-tetracyclines using reagents which are more environmentally friendly thus giving less effluent problems, thereby affording a simpler purification. These compounds have a wide therapeutical application.

4-(Des-dimethylamino)-tetracyclines do not present the anti-bacteriological activity which is typical of tetracyclines but have a remarkable therapeutical activity as described in the following patent applications: treatment of diabetes and other disfunctions (U.S. Pat. No. 5,532,227, EP 599,397); treatment of inflammatory diseases (U.S. Pat. No. 5,523, 297, WO 9,808,480); treatment of arthritis, ulcers and muscular diseases (EP 435,362, 586,020); prophylactic treatment for diseases of the teeth and gums (AU 9,338,201, WO 9,213,515). These compounds can be administered alone or jointly with other drugs.

Processes for the preparation of 4-(des-dimethylamino)-tetracyclines described in the literature employ a mixture of zinc and acetic acid. An excess of the reducing agent, i.e. zinc, is used to achieve the elimination of the C-4 amino group, starting from trialkylammonium salts of the tetracycline to be reduced (J. Amer. Chem. Soc., 80, 1654 (1958)). The acid addition salts can also be reduced by zinc and acetic acid, yielding the 4-(des-dimethylamino)-tetracyclines, but in this particular case there will be a tendency for the product to have the 6-hydroxy group also reduced (J. Amer. Chem. Soc. 76, 3568 (1954)).

This method is problematic with respect to the level of waste discharge, which is potentially polluting, and effluents produced during the industrial preparation of 4-(des-dimethylamino)-tetracyclines resulting from the presence of unconsumed metallic zinc and elimination of zinc salts.

The presence of zinc can also be problematic with respect to the purification of the product manufactured by this process due to the high capacity of tetracycline derivatives to form stable chelates with metals. Thus, in the prior art, significant amounts of zinc can remain in the final 4-(des-dimethylamino)-tetracycline. It should be noted that one of the most significant indications for the use of 4-(des-dimethylamino)-tetracyclines is as metalloprotease (MP) inhibitors (EP 435,362A). The mode of action of these compounds involves complexing with zinc in the enzyme so that presence of zinc in the 4-(des-dimethylamino)-tetracyclines can have a detrimental effect on activity.

The aim of the present invention is to find a clean process which allows elimination of the C-4 substituent, without using zinc, thus overcoming both the environmental and purification problems.

In the prior art processes related to the synthesis of 4-(des-dimethylamino)-tetracyclines, the tetracycline to be reduced is methylated in a first stage with methyl iodide and in a second stage the trimethylammonium salt is reduced with a mixture containing zinc and acetic acid.

The method for the synthesis of 4-(des-dimethylamino)-tetracyclines described in the present invention affords the elimination of the C-4 dimethylamino group, its advantage over the prior art method being that it does not use zinc. The reduction of the trimethylammonium salts of tetracycline, using this method, is carried out electrochemically in an aqueous solution. In this way, the problems associated with the use of zinc and acetic acid are eliminated. The final products, which do not have amphoteric properties like the known tetracyclines, may thus be isolated by extraction by organic solvents, giving compounds in good yield and with a purity over 97%.

The present invention refers to a process for the preparation of 4-(des-dimethylamino)-tetracyclines. The tetracycline to be reduced is treated with an alkylating agent, preferably methyl iodide in an organic solvent, preferably acetone, the trialkylammonium salt resulting thereby being electrolytically reduced in an aqueous pH acid solution. The pH of the solution is kept between 0.5 and 5.0, preferably between 1.0 and 3.0. The tetracycline reduced in C-4 is thus obtained, having a purity of typically over 97% by high performance liquid chromatography (HPLC).

In a first stage and, according to the methods hereinafter described, the tetracycline to be reduced is suspended in an organic solvent, preferably acetone, and the suspension is maintained between 25 and 40° C., preferably between 30 and 33° C., although other temperatures outside this range may be employed. The alkylating agent, preferably methyl iodide, is subsequently added. The reaction mixture is stirred at the above temperature ranges during the period of time necessary to obtain alkylation of the nitrogen atom at C-4. Typically, the reaction is complete between 48 and 72 hours at 30–33° C. The course of the reaction can be controlled by HPLC, or by any other suitable method. The excess of the methylating agent is removed by distillation under atmospheric pressure. The solvent is reduced to half of the volume or less, by distillation. The iodide salt of the tetracycline alkylated at C-4 is isolated by direct precipitation of the solution in an ether, such as isopropyl ether, or alternatively by dissolving the residue in a lower molecular weight alcohol, followed by the addition of a non-solvent such as, for example, ethyl or isopropyl ether.

The trimethylammonium salt of the tetracycline is dissolved in water and an acid is added to maintain the solution at an acid pH. The acid used to that effect is preferably acetic acid at a concentration of 30 to 70%, preferably from 50 to 60%. The solution is then purged with an inert gas, such as nitrogen or argon, and kept in an electrochemical cell under an inert atmosphere, to which an electrolyte, used to allow the passage of the electric current, is added. The referred electrolyte can be a sodium or a potassium salt, such as chloride, bromide, iodide, or acetate, preferably potassium chloride in a concentration between 0.01 and 1 mol, the preferred range being from 0.1 to 0.5 mol. The construction materials of the electrodes, used in the electrochemical cell for application of the electric current to the solution, can be chosen from platinum, mercury, stainless steel or carbon, the preferred electrodes being platinum and mercury.

After placing the solution of the tetracycline salt in a temperature range between 10 and 40° C., preferably between 20 and 25° C., a direct current between 0.5 and 1.5 volts is applied between the two electrodes of the cell, preferably between 1 and 1.15 volts. The potential is maintained for a period of time sufficient to allow reduction of the trimethylammonium salt of the tetracycline. The course of the reaction can be controlled by HPLC. The end point of the reaction is conveniently reached after 2 to 6 hours, although faster or slower reaction times may be possible at higher and lower temperatures respectively.

After the reaction is complete, an aqueous solution containing hydrochloric acid (0.5 to 2N) is added, as well as an organic solvent wherein the 4-(des-dimethylamino)-tetracyclines are soluble, such as, among others, chloroform, dichloromethane or ethyl acetate, preferably dichloromethane, so as to allow extraction of the reduced tetracycline from the aqueous phase. The organic phase is washed with diluted hydrochloric acid and subsequently with water.

After the solution is dried and concentrated under reduced pressure, the residual acetic acid can be azeotropically distilled with, for example, cyclohexane. The 4-(desdimethylamino)-tetracycline is obtained after drying the mixture at 25–40° C., as a yellow solid the purity of which is typically more than 97% by HPLC. The 4-(desdimethylamino)-tetracycline can also be isolated by crystallisation with acetone after removal of the acetic acid.

The following examples serve only to illustrate the different aspects of the invention and are not in any way to be considered as a limitation of the specification and claims thereof.

EXAMPLE 1

Preparation of 1,4,4α,5,5α,6,11,12α-octahydro-3,10,12,12α-tetrahydroxy-1,11-dioxonaphthacene-2-carboxamide.

10 g of 4-dimethylamino-1,4,4α,5,5α,6,11,12α-octahydro-3,10,12,12α-tetrahydroxy-1,11-dioxonaphthacene-2-carboxamide were suspended in 100 ml of acetone. The reaction mixture was heated to 30–33° C., followed by the addition of 13.7 ml of methyl iodide. After stirring for 72 hours at room temperature, the product dissolved completely and the reaction was complete after a further 24 hour period. The solvent was distilled under atmospheric pressure and the residue was then dissolved in 110 ml of acetone. The solution was evaporated to half of its volume and thereafter added during 1 hour to 700 ml of ethyl ether, after which it precipitated. The iodide salt of the tetracycline, trimethylated at the 4 nitrogen, was then dried at 35–40° C., yielding the desired compound with a purity of about 97% by HPLC.

10 mg of 4-trimethylammonium-1,4,4α,5,5α,6, 11,12α-octahydro-3,10,12,12α-tetrahydroxy-1,11-dioxonaphthacene-2-carboxamide iodide and 38 mg of potassium chloride were dissolved in 5 ml of an aqueous acetic acid solution (50%). This solution was placed into the compartment of an electrochemical cell, equipped with a dropping mercury electrode and a secondary platinum coated electrode. A reference electrode (calomel), immersed in a solution containing 0.1 mol of potassium chloride in 50% aqueous acetic acid, was placed in the other compartment of the referred cell. The two compartments of the cell were separated by a porous glass membrane. The solutions were purged with nitrogen for about 20 minutes. A continuous current of –0.85 volts in relation to the calomel electrode was then applied for about 2 hours at room temperature. The solution was then acidified with 0.5 ml of 2N hydrochloric acid and extracted three times with 5 ml of dichloromethane. The combined organic phases were subsequently extracted with 0.5N hydrochloric acid and dried with anhydrous sodium sulfate. The title compound was isolated after distillation of the solvent at reduced pressure and dried at 35–40° C., under the form of a yellow solid with a purity of greater than 97% by HPLC.

EXAMPLE 2

Alternative method for the preparation of 1,4,4α,5,5α,6,11,12α-octahydro-3,10,12,12α-tetrahydroxy-1,11-dioxonaphthacene-2-carboxamide.

500 mg of 4-trimethylamino-1,4,4α,5,5α,6,11,12α-octahydro-3,10,12,12α-tetrahydroxy-1,11-dioxonaphthacene-2-carboxamide were dissolved in a mixture containing water/acetic acid (120 ml:180 ml), to which 7.5 g of potassium chloride were added. The reaction mixture was degassed and kept under nitrogen atmosphere during the course of the reaction. After 30 minutes, a potential difference of 1.15 volts was applied between the two stainless steel electrodes and the potential was kept constant for about 6 hours. After the reaction was complete, 5 ml of 1N hydrochloric acid and 100 ml of dichloromethane were added. The phases were separated and the aqueous phase was extracted twice with 50 ml of dichloromethane. The organic phases were combined and extracted three times with 20 ml of aqueous 0.5N hydrochloric acid. The organic phase was dried with anhydrous sodium sulfate and evaporated under reduced pressure. The residual acetic acid was removed by co-distillation with cyclohexane. The yellow solid thus obtained was dried under vacuum between 30 and 35° C., yielding the title compound with a purity more than 97% by HPLC.

EXAMPLE 3

Preparation of 1,4,4α5,5α6,11,12α-octahydro-3,5,10,12,12α-pentahydroxy-6α-methyl-1,11-dioxonaphthacene-2-carboxamide.

10 g of doxycycline were dispersed in 100 ml of acetone. The reaction mixture was placed in a thermostatic bath at 30–33° C., and 13 ml of methyl iodide were added. No change in colour or temperature of the suspension was observed. After stirring for 48 hours at room temperature total dissolution was observed and the reaction was complete after an additional 24 hour period (conversion >96% by HPLC). The solvent was distilled under atmospheric pressure, and the residue was dissolved in methanol (35 ml) and precipitated with ethyl ether (700 ml). The yellow solid was filtered, washed with ethyl ether and dried at 35–40° C., yielding the trimethylammonium salt with a purity greater than 96% by HPLC.

200 mg of 4-trimethylammonium-1,4,4α5,5α6,11,12α-octahydro-3,5,10,12,12α-pentahydroxy-6α-methyl-1,11-dioxonaphthacene-2-carboxamide iodide were dissolved in a mixture of water/acetic acid (48 ml:72 ml), to which 3 g of potassium chloride were added. The reaction mixture was degassed and kept under nitrogen atmosphere during the course of the reaction. After 30 minutes, a potential difference of 1.15 volts was applied between the two stainless steel electrodes and the potency was kept constant for about 6 hours. After the reaction was complete, 5 ml of 1N hydrochloric acid and 60 ml of dichloromethane were added. The phases were separated and the aqueous phase was extracted twice each with 60 ml of dichloromethane. The organic phases were combined and extracted three times with dilute aqueous hydrochloric acid. The organic phase was dried with anhydrous sodium sulfate and evaporated under reduced pressure. The residual acetic acid was chased with cyclohexane. The yellow solid thus obtained was dried at room temperature under vacuum, yielding the title compound with a purity greater than 98% by HPLC.

What is claimed is:

1. A process for the preparation of a 4-(desdimethylamino)-tetracyclines by reduction of an ammonium salt of a tetracycline, characterised in that the reduction is effected electrochemically.

2. A process according to claim 1, wherein the reduction is effected on a corresponding trimethylammonium salt.

3. A process according to claim 1, wherein the salt is in aqueous acidic solution.

4. A process according to claim 3, wherein the acidic solution contains acetic acid.

5. A process according to claim 4, wherein the reduction is effected on the trimethylammonium salt.

6. A process according to claim 5, wherein said the solution contains sodium acetate, potassium chloride, potassium iodide, potassium bromide, sodium chloride, sodium iodide, sodium bromide or any mixture or two or more thereof, in a concentration of 0.01 to 1 molar.

7. A process according to claim 6, wherein the reduction is effected using a direct current of substantially constant potential.

8. A process according to claim 7, wherein the potential is from 0.5 to 1.5 volts.

9. A process according to claim 8, wherein there is used at least one electrode of platinum, mercury, stainless steel or carbon.

10. A process according to claim 1, wherein the solutin also contains another electrolyte.

11. A process according to claim 10, wherein said electrolyte is sodium acetate, potassium chloride, potassium iodide, potassium bromide, sodium chloride, sodium iodide, sodium bromide or any mixture of two or more thereof, in a concentration of 0.01 to 1 molar.

12. A process according to claim 1, wherein the reduction is effected using a direct current of substantially constant potential.

13. A process according to claim 12, wherein the potential is from 0.5 to 1.5 volts.

14. A process according to claim 1, wherein there is used at least one electrode of platinum, mercury, stainless steel or carbon.

* * * * *